United States Patent [19]

Ron

[11] Patent Number: 5,530,492
[45] Date of Patent: Jun. 25, 1996

[54] OPHTHALMOLOGICAL INSTRUMENT FOR PRODUCING DICHOPTIC STIMULI ON A VISUAL DISPLAY TERMINAL

[75] Inventor: Samuel Ron, Ramat Hasharon, Israel

[73] Assignee: Medoptics Limited, Israel

[21] Appl. No.: 34,717

[22] Filed: Mar. 22, 1993

[51] Int. Cl.⁶ .............................. A61B 3/02; A61B 3/08; A61B 3/09; H04N 13/04
[52] U.S. Cl. .......................... 351/201; 351/222; 351/232; 351/240; 351/243; 351/246; 348/54
[58] Field of Search ............................. 351/175, 41, 200, 351/201, 222, 223, 232, 233, 237, 239, 240, 243, 246; 358/92

[56] References Cited

U.S. PATENT DOCUMENTS

| | | | |
|---|---|---|---|
| 2,206,303 | 7/1940 | Neumeueller et al. | 351/232 |
| 4,870,486 | 9/1989 | Nakagawa et al. | 358/92 |
| 5,076,665 | 12/1991 | Petersen | 359/811 X |
| 5,143,081 | 9/1992 | Young et al. | 128/745 X |
| 5,204,702 | 4/1993 | Shapiro | 351/175 |

FOREIGN PATENT DOCUMENTS

WO9100050  1/1991  WIPO ................. 351/243

*Primary Examiner*—William L. Sikes
*Assistant Examiner*—Hung Xuan Dang
*Attorney, Agent, or Firm*—Leonard Bloom

[57] ABSTRACT

A method and system for presenting two successive images on a video display unit as a dichoptic stimulus of substantially equal intensity, wherein a first image is displayed at a predetermined intensity so as to be seen by a first eye of an observer only, an optical shutter being used to prevent the displayed image from reaching the second eye of the observer. The first image is then extinguished and the state of the optical shutter reversed so that the first eye can no longer see the video display unit whilst a second image is presented to the second eye. In order to prevent the second eye from seeing an after image of the first image, a neutral density filter or polarizer is disposed within the light path and the second image is illuminated at a correspondingly higher intensity so as to compensate for the attenuation factor of the neutral density filter or polarizer. Such a method may be employed to measure the dark vergence of the observer which has been found to be a major factor in determining fatigue of computer operators, in order that corrective action may be taken so that the angle subtended by an image on the computer screen at the eyes of the observer may be adjusted to the angle of dark vergence. Such corrective action may be provided by individually tailored prismatic spectacles.

31 Claims, 11 Drawing Sheets

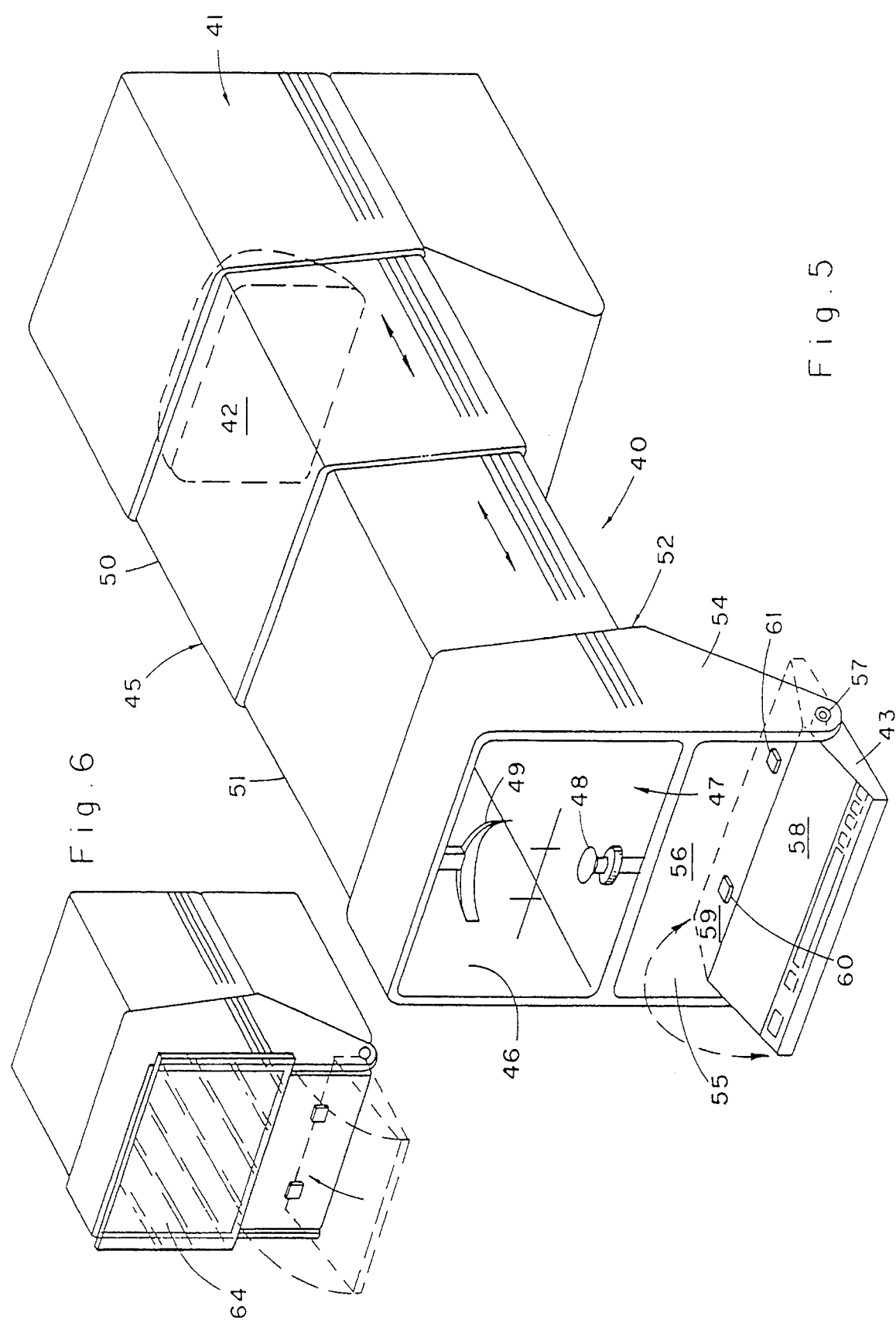

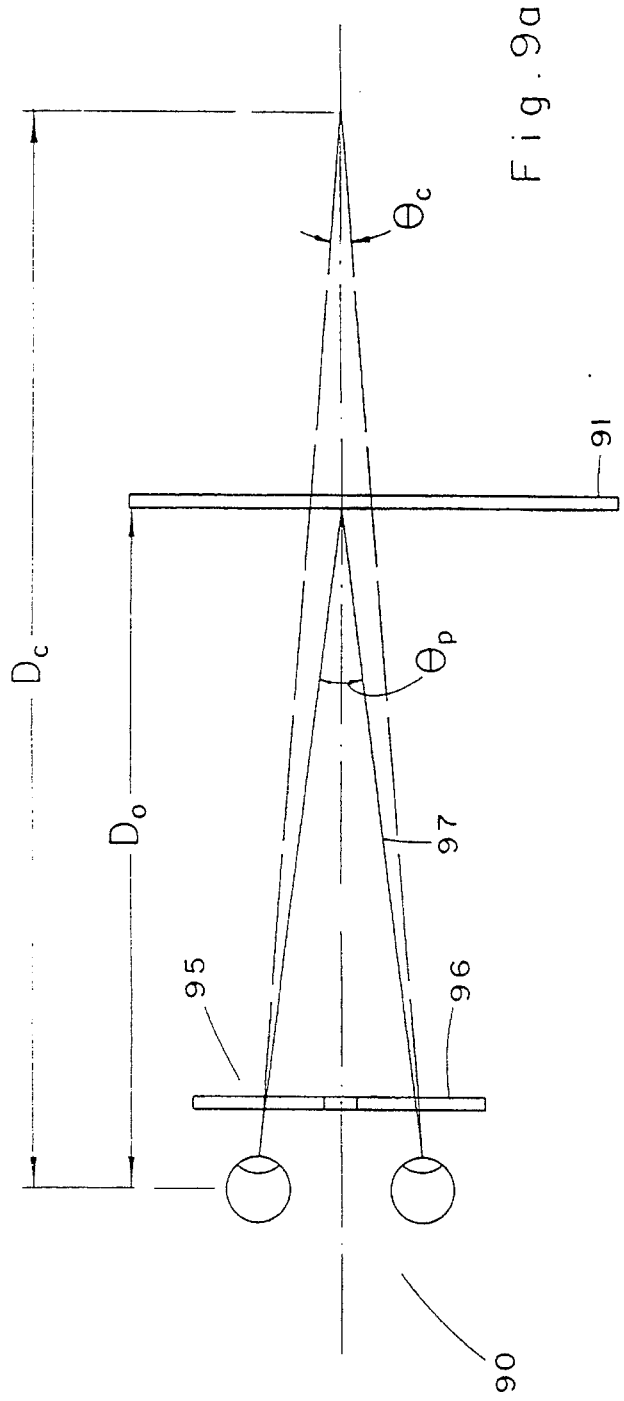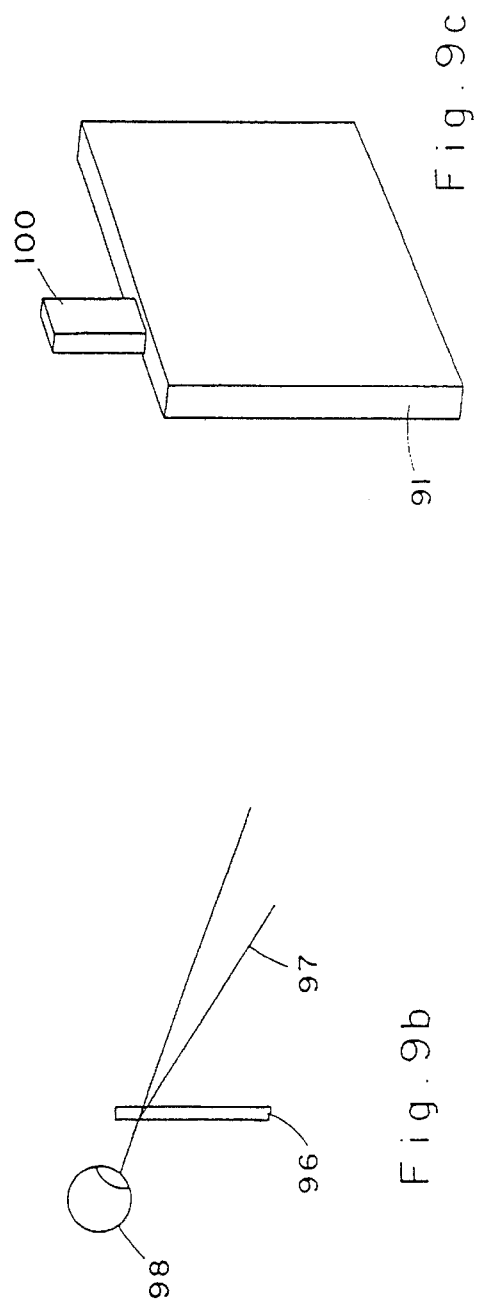

OPHTHALMOLOGICAL INSTRUMENT FOR PRODUCING DICHOPTIC STIMULI ON A VISUAL DISPLAY TERMINAL

FIELD OF THE INVENTION

This invention relates to a method and apparatus for presenting dichoptic stimuli on a video display unit (VDU). In particular, it relates to the use of such a method and apparatus for measuring the dark vergence of an observer, especially a computer operator, whereupon suitable remedial action can be taken, if required, so as to reduce the effects of operator fatigue.

BACKGROUND OF THE INVENTION

In this discussion of prior art, reference will be made to the following articles:

1. Wolfgang Jaschinski-Kruza in "Eyestrain in VDU Users: Viewing Distance and the Resting Position of Ocular Muscles" in Human Factors, 1991, 33(1), 69–83.
2. D. Alfred Owens, "The Resting State of the Eyes" (1984) American Scientist, 72, 378–387.
3. Wolfgang Jaschinski-Kruza, "Effects of Stimulus Distance on Measurements of Dark Convergence" Ophthalmic and Physiological Optics, 10, 243–251.

It was long thought that, when at rest, a person's eyes are focused at infinity. That this view has now been shown to be erroneous is discussed at length by Jaschinski-Kruza[1] who shows that, contrary to the traditional view cited above, intermediate positions of accommodation and convergence are generally observed in a visually featureless environment.

D. Alfred Owens[2] shows that visual perception under adverse conditions is, to some extent, dependent on the natural tonus of the eye muscles whereupon whenever visual conditions are degraded, the eyes tend to shift involuntarily to the individual's "resting" distance.

As is well known, the convexity of the crystalline lens on the front of the eye is adjusted by the ciliary muscles in order to focus on objects at different distances from the eye. At the same time, the eyes' axes are rotated by the extraocular muscles so that a person's eyes are directed towards an object of interest. The closer the object of interest is to the eyes of the observer, the greater is the required rotation of the eyes of the observer by the extraocular muscles. It was once assumed that, since minimum rotation is required when the eye is focused at infinity, viewing any object closer than infinity strains the extraocular muscles thereby causing eyestrain and related fatigue.

However, as reported by D. Alfred Owens[2] and Jaschinski-Kruza [1,3], in fact, when most subjects look into a homogeneous field without any fixation stimulus, e.g. into darkness, their visual axes converge to a certain intermediate distance. This distance is variably referred to by the terms "dark convergence", "tonic vergence", "resting position of convergence" and is referred to throughout the remainder of this specification and claims under the term "dark vergence".

Jaschinski-Kruza[1] reports that the more distant a subject's dark vergence, the greater is the visual strain at a 50 cm viewing distance. Specifically, a marked difference between the distance of a subject to a VDU from the characteristic dark vergence of the subject, the more pronounced will be the resulting operator fatigue consequent to extended use of the VDU. This having been shown to be the case, it is clearly desirable to adjust, as far as possible, an operator's distance from a VDU so as to be equal to the dark vergence of the operator. D. Alfred Owens[2] measured the dark vergence of 220 college students all of whom either did not require correction spectacles or were wearing their normal spectacles and were told to "relax" their eyes while their accommodation was measured in total darkness. On average, subjects focused for a distance of approximately 67 cm in the dark. While a few (about 1%) focused to optical infinity, as predicted by classical theory, others focused as close as 25 cm.

Jaschinski-Kruza[1] shows the correlation between variation in viewing distance from an operator's dark vergence and operator fatigue. When the subjects were free to adjust the viewing distance, they were most comfortable when the distances thus chosen were between 51 and 99 cm with characters 5 mm tall. This correlates well with the measured average dark vergence of 67 cm reported by D. Alfred Owens[2].

From the foregoing, two things are clear: first, dark vergence varies between limits from one subject to another; and the optimal comfort distance from an operator to a video display unit is influenced by the operator's dark vergence. Thus, the question arises as to how dark vergence may be measured for a particular subject.

As reported by Jaschinski-Kruza[3], dark vergence is typically measured psychophysically by aligning two dichoptic stimuli which are briefly flashed in a dark surround. Jaschinski-Kruza[3] reports the effect of varying the viewing distance of the stimulus and further reports that the measured dark vergence was biased towards the actual viewing distance of the stimuli: this effect being stronger with bar stimuli than with point-and-line stimuli. The subject's foreknowledge of the viewing distance had a small but nevertheless significant effect; whilst the size of the nonius bars had none. The method employed by Jaschinski-Kruza is based on the coincidence of nonius bars whereby two vertical light bars are presented dichoptically on a dark surround, dichoptic separation being achieved by red and green filters. The bars were exposed for 100 ms every 2.5 s, the mutual separation between the bars being adjusted in a staircase procedure until perceived by the observers as being vertically aligned.

According to an alternative method, a bright red light-emitting diode (LED) was flashed in a dark surround for 100 ms at 2.5 s intervals. A Maddox rod and a rotary prism were placed in front of the observer's left eye, the prism being rotated by the observer to a position wherein the red point seen by the right eye coincided with the vertical line of light visible through the Maddox rod in front of the left eye. Suitable measurements and calculations were then performed in order to determine the dark vergence of the subject.

Although the correlation between dark vergence and eyestrain have been clearly established and although known methods for determining dark vergence are based on the alignment of dichoptic stimuli, no simple instrument has been provided which permits the presentation of dichoptic stimuli on a VDU. The reason for this probably lies in the fact that, in order to present dichoptic stimuli to the eyes, each eye must be forced to see its own image and only its own image. If, to the contrary, one eye sees the image (even partially) which was presented to its fellow eye, then the whole basis of the psychophysical measurement is destroyed. Herein lies the problem with using a VDU to present dichoptic stimuli because, as is known, the pixels of which the VDU screen is composed, continue to phosphoresce even when they are no longer subjected to a source of electric power. Consequently, if a first image is displayed on a VDU by illuminating certain pixels thereof in order that only one eye can see the image and then the image is extinguished prior to illuminating other pixels, constituting a second image for viewing by the fellow eye, then the fellow eye will see not only its own image but will also see the after image of the first image owing to the residual phosphorescence of the pixels. If, in order to avoid this, a sufficiently long time period is allowed to elapse between the successive presentation of the successive images then, whilst the problem of residual after image will be avoided, the two images will no longer be dichoptic. In other words, the obvious solution to avoiding the effect of after image, namely to lengthen the time period between the presentation on the VDU of successive images, militates against the two images being seen by the eyes as a dichotic stimulus.

No solution to this problem has been reported, so far as is known, in either the scientific or the patent literature.

SUMMARY OF THE INVENTION

It is a principal object of the invention to provide a method and apparatus for presenting dichoptic stimuli on a video display unit.

It is a further object of the invention to provide a method and apparatus for determining the distance of dark vergence of an operator using a video display unit.

Yet another object of the invention is to provide correction spectacles for correcting for dark vergence of a user, particularly so as to reduce operator fatigue of computer personnel and other users of video display units.

According to a first aspect of the invention there is provided a method for presenting two successive images on a video display unit as a dichoptic stimulus of substantially equal intensity, comprising the steps of:

(a) displaying a first one of the images at a predetermined intensity on the video display unit so as to be seen by a first eye of an observer only, (b) suppressing any after image of the first image to a second eye of the observer, and (c) displaying a second one of the images on the video display unit so as to be seen by the second eye of the observer only at said predetermined intensity.

Such an approach for presenting a dichoptic stimulus on a video display unit may be employed in a method for determining a dark vergence of an observer, comprising the steps of:

(a) measuring an interpupillary distance of the observer, (b) determining a visual threshold of the observer, (c) presenting a series of two successive images on a video display unit as a dichoptic stimulus of substantially equal intensity such that a first one of the images is stationary and a second one of the images may be moved by illuminating different pixels of the video display unit, (d) for each series of images presented on the video display unit, moving the second one of the images until both images appear to the observer to be aligned, (e) measuring any actual displacement between the two images, and (f) calculating a distance of dark vergence according to the formula:

$$D_c = \frac{P_d D_o}{P_d - f(T)}$$

where:

$D_c$ is the distance of dark vergence;

$P_d$ is the interpupillary distance;

$D_o$ is a distance from the observer to a viewing plane of the video display unit; and f(T) is a function of the measured displacement T between the two dichoptic images.

Having thus determined the distance of dark vergence of the observer, it is clearly desirable to ensure that the distance of the light path from the displayed image to the operator be adjusted to the measured distance of dark vergence of the observer. This can be done either by moving the operator relative to the video display unit until the two distances are substantially the same or, alternatively, by bending the light path using prismatic spectacles so that the resulting image appears to emanate from the plane of dark vergence of the observer.

BRIEF DESCRIPTION OF THE DRAWINGS

In order to understand the invention and to see how the same may be carried out in practice, some preferred embodiments will now be described, by way of non-limiting example only, with reference to the accompanying drawings, in which:

FIG. 5 is a pictorial representation of an apparatus according to the invention for determining the distance of dark vergence of an observer;

FIG. 6 is a detail of a telescopic tunnel used in the apparatus shown in FIG. 5 when in a fully closed position;

FIGS. 9a, 9b and 9c are schematic representations of correction spectacles and an alarm unit for use by a computer operator sitting in front of a computer screen for correcting for dark vergence.

DETAILED DESCRIPTION OF PREFERRED EMBODIMENTS

Figure 1A:
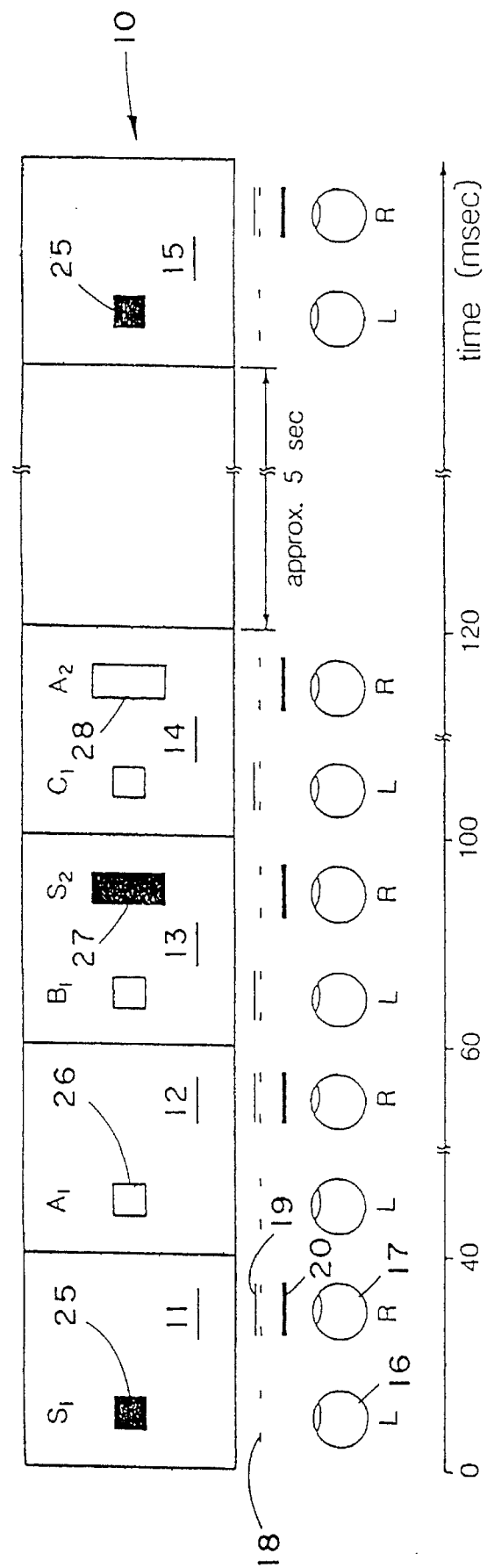
FIG. 1a is a timing diagram showing, pictorially, a series of dichoptic images presented to respective eyes of an observer.

FIG. 1a shows schematically a computer screen 10 for displaying, during successive frames 11, 12, 13, 14 and 15 respective images to a corresponding eye of an observer so that successive pairs of images are perceived by the observer as a dichoptic stimulus. In respect of each of the frames 11 to 15 there is shown a pair of eyes 16 and 17 (constituting first and second eyes, respectively) and a corresponding pair of optical shutters 18 and 19 between the computer screen 10 and the eyes of the observer and constituting, respectively, first and second optical shutters. Disposed between the second optical shutter 19 and the second eye 17 of the observer is a neutral density filter 20 having a known attenuation factor.

During the first frame 11 the first optical shutter 18 is opened and the second optical shutter 19 is shut so as to inhibit the second eye 17 from seeing an image seen by the first eye 16. At the same time, a plurality of pixels on the computer screen 10 are illuminated so as to present to the first eye 16 an image 25. The image 25 is presented to the first eye 16 for a period of approximately 40 ms, whereafter the image 25 is extinguished. Owing to the persistence of phosphorescence of the computer screen 10, an after image 26 remains on the computer screen 10 even though the pixels constituting the first image 25 are no longer illuminated. After a further period of 20 ms, the first optical shutter 18 is closed, the second optical shutter 19 is opened and a second image 27 is illuminated on the computer screen 10 as shown in the third frame 13. During the third frame 13, the first eye 16 cannot see the computer screen 10 owing to the optical shutter 18 being closed, whilst the second eye 17 sees the second image 27 through the optical shutter 19 (which is open) and the neutral density filter 20. However, it will be understood that the principle of dichoptic stimulation is based on the fact that the first eye 16 sees an after image of the stimulus 25 even when the first optical shutter 18 is closed. In order that the second image 27 may be seen by the second eye 17 at the same intensity as the first image 25 was seen by the first eye 16, the luminosity of the pixels constituting the second image 27 is increased by the attenuation factor of the neutral density filter 20. It should be noted that throughout the specification and appended claims, the term "attenuation factor" denotes a number greater than unity enumerating the factor by which the luminosity is reduced by the neutral density filter 20.

During the third frame 13, although the first eye 16 is inhibited from seeing the residual after image 26 owing to the presence of the closed optical shutter 18, steps must be taken to ensure that the second eye 17 does not see the after image 26 even though the second optical shutter 20 is now open. To this end, the attenuation factor of the neutral density filter 20 is selected so that the resulting luminosity of the after image 26 is below the visual threshold of the observer. Thus, during the third frame 13, the second eye 17 sees only the second image 27 whilst the first eye 16 continues to "see" the first image 25 owing to the after image of the visual system of the eye. Consequently, the two images 25 and 27 appear to the eyes 16 and 17 as a pair of dichoptic stimuli.

During the fourth frame 14, the second image 27 is extinguished so as to leave a residual after image 28 on the computer screen 10 which is seen by the second eye 17 for a period of approximately 20 ms during which time the second eye 17 can, of course, still no longer see the after image 26 of the first image 25 owing to the neutral density filter 20 and the fact that the after image 26 will, by now, have decayed even more.

After a further period of approximately 5 sec., another sequence of dichoptic stimuli is presented, as represented by the first image 25 in the fifth frame 15.

Figure 1B:
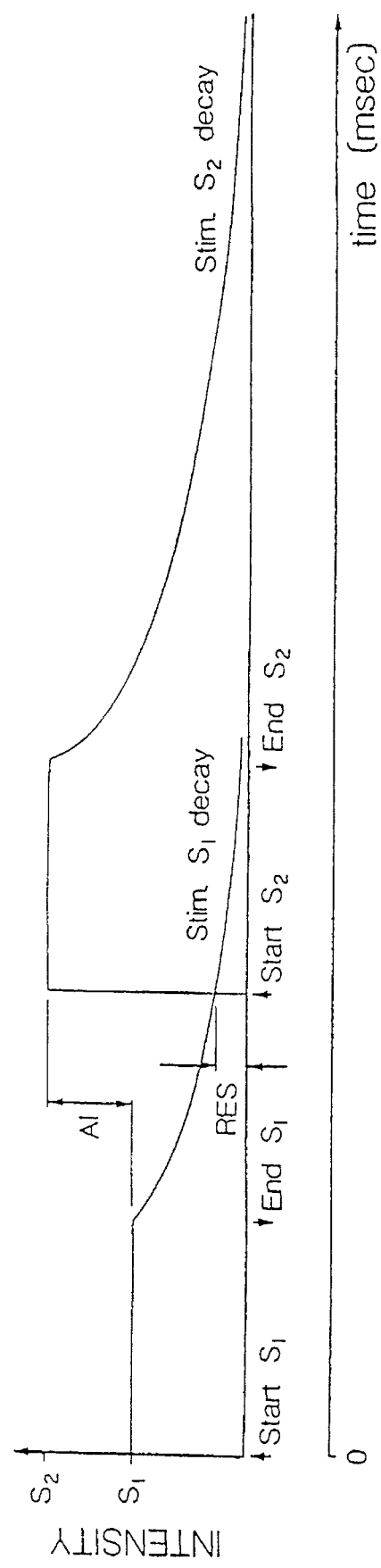
FIGS. 1b and 1c show intensity decay curves in respect of a single pair and a series of dichoptic stimuli, respectively.

Referring now to FIG. 1*b* there is shown a graphical representation of the intensity of the first and second images 25 and 27, respectively. Thus, it will be seen, that the first image 25 is displayed at an intensity $S_1$ and that, upon being extinguished at the end of the first frame 11, it decays exponentially so as to have a residual intensity, Res, at the start of the third frame 13 wherein the second image 27 is displayed to the second eye 17 at an intensity $S_2$ being equal to the first intensity $S_1$ multiplied by the attenuation factor of the neutral density filter 20. At the end of the third frame 13, the second image 27 is extinguished and it, too, decays until the next sequence of dichoptic stimuli is presented.

Figure 1C:
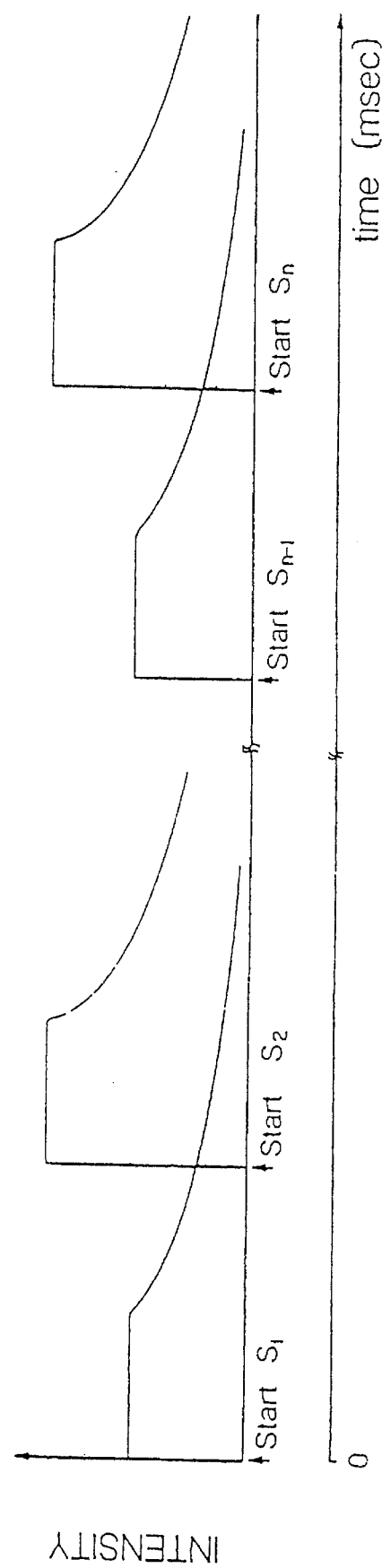

FIG. 1*c* is a graphical representation showing the intensity of respective images in respect of a series of dichoptic stimuli presented on the computer screen 10 in accordance with the method described above.

Figures 2A, 2B:
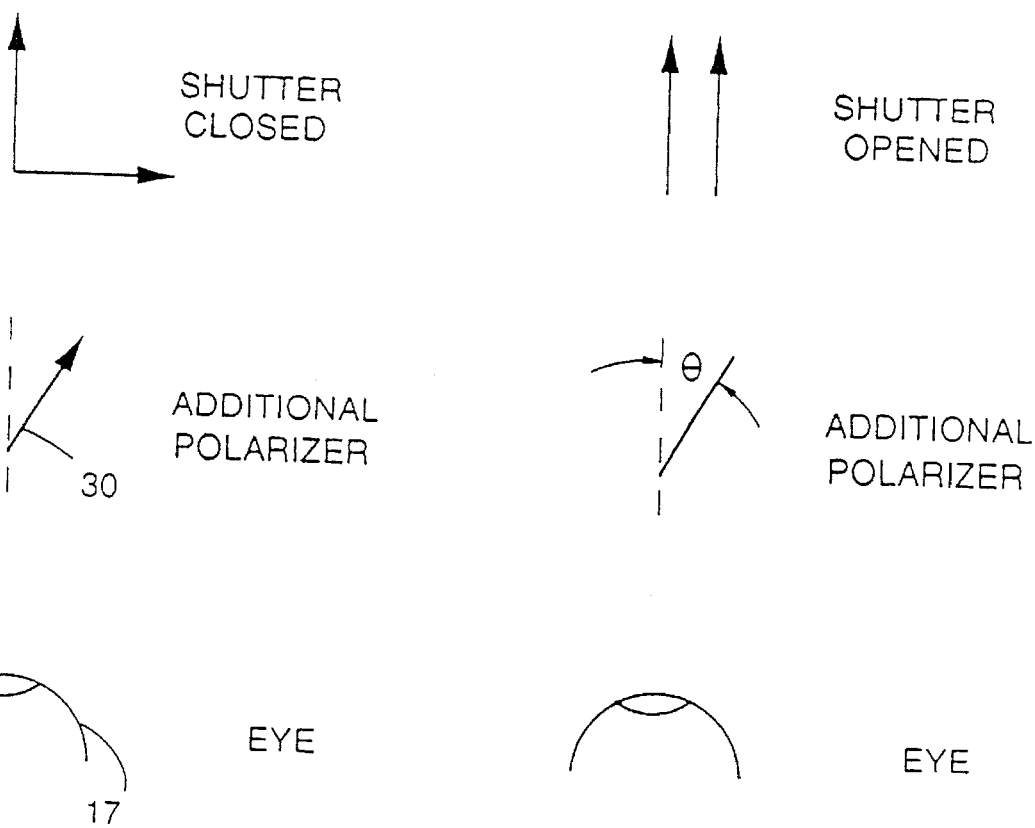
FIGS. 2a and 2b show schematically a method for attenuating an image using a polarizing element.

FIG. 2 shows schematically an alternative approach for attenuating the intensity of the after image 26 of the first image 25 so as to prevent its being seen by the second eye 17 when the second optical shutter 19 is opened. Instead of employing the neutral density filter 20, there is provided instead a polarizer depicted schematically as 30 having a polarization angle θ. The magnitude of the angle θ determines the effective attenuation factor of the polarizer 30.

Figure 3A:
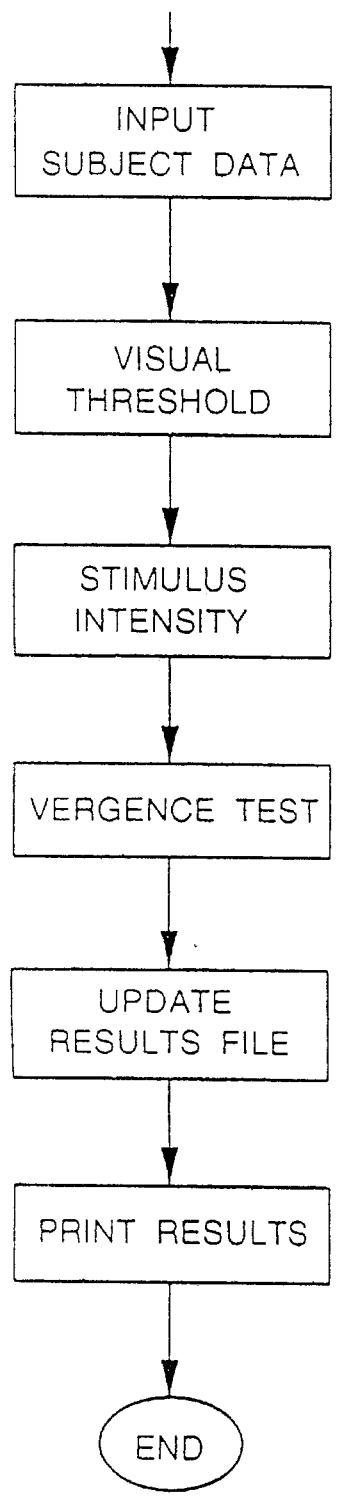
FIGS. 3a, 3b and 3c are flow diagrams showing the principal operating steps in determining a distance of dark vergence of an observer.
Figure 3C:
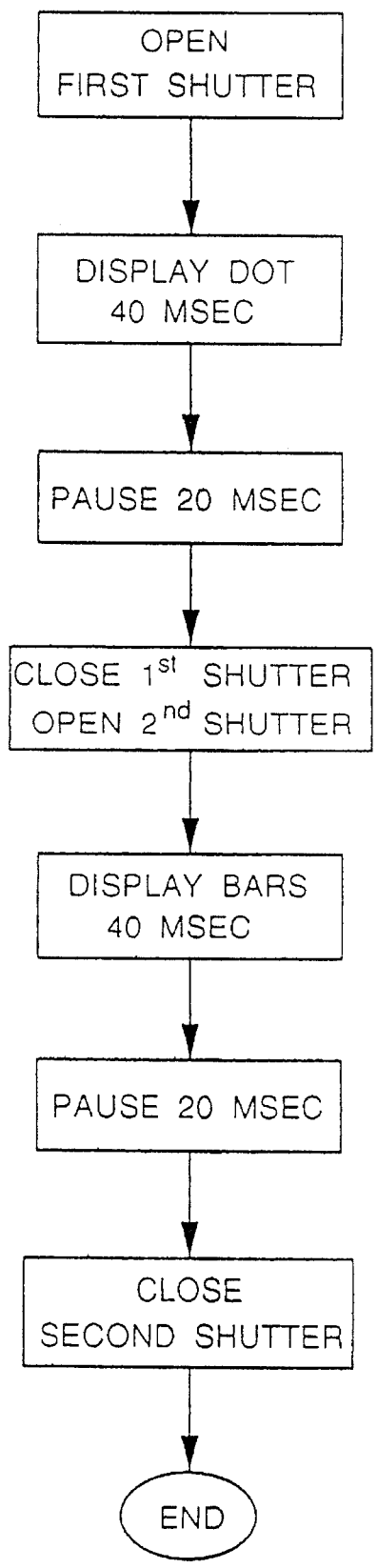
Figure 3B:
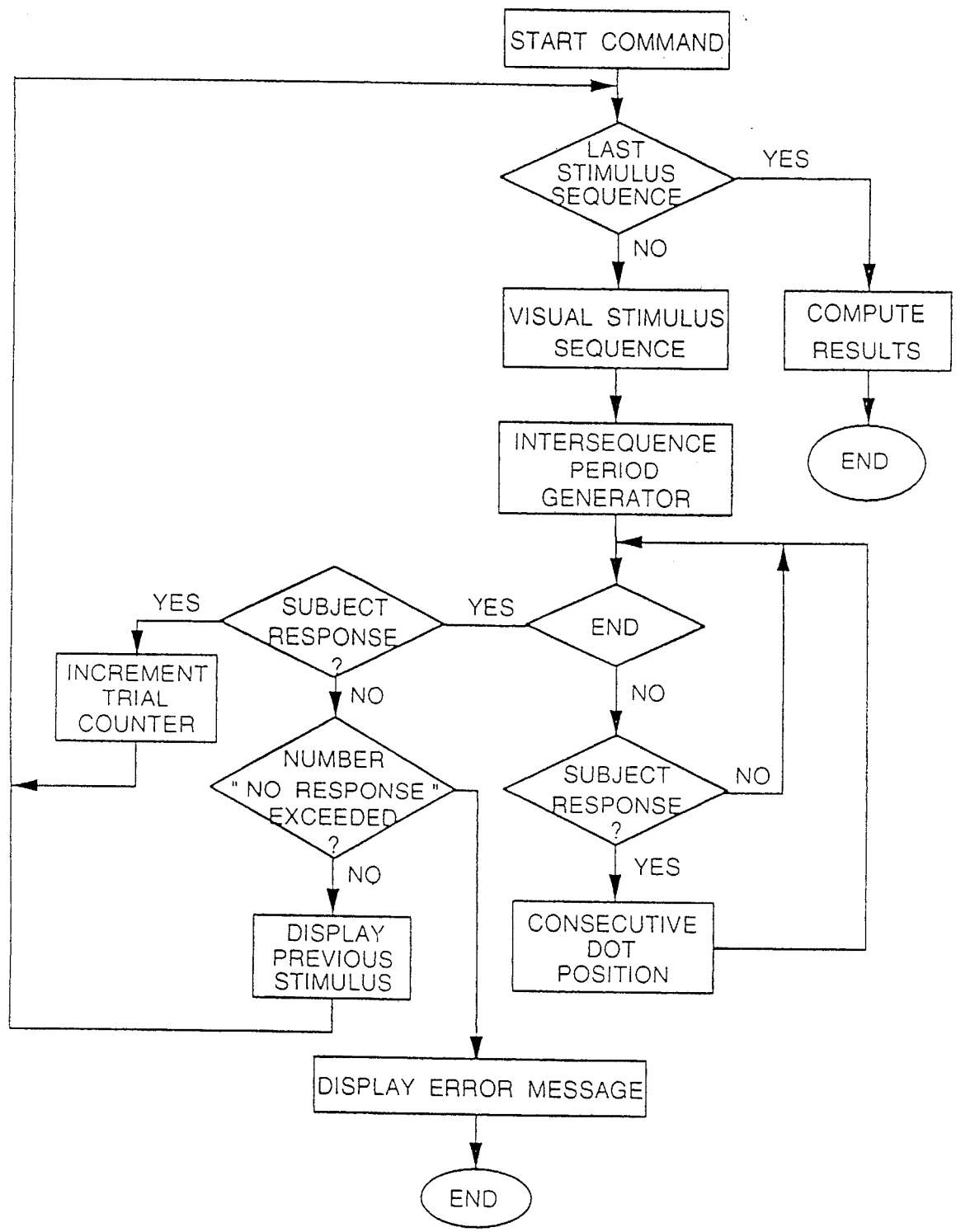

Referring now to FIGS. 3*a* to 3*c* there are shown respective flow diagrams of the principal operating steps in a method for determining the dark vergence of an observer based on the principle of displaying dichoptic stimuli on a video display unit as described above with particular reference to FIGS. 1*a* to 1*c* of the drawings. The method for determining dark vergence involves a sequence of tests wherein successive pairs of dichoptic stimuli are presented on a computer screen, the observer indicating any apparent misalignment between the first and second images constituting each pair of dichoptic stimuli, the apparent misalignment being compensated for until the two images appear aligned. When the two images appear to be aligned to the observer, this means that the images subtend the angle of vergence at the observer's eyes or, in other words, that the horizontal extraocular muscles are completely relaxed. Any actual misalignment between the two images may now be used to calculate the dark vergence of the observer.

Thus, as shown in FIG. 3*a*, at the start of the test various constant data relating to each observer are measured and recorded. Specifically, there is stored an identification in respect of the observer, his inter-pupillary distance is measured and recorded and likewise his visual threshold is measured and recorded. Thereafter, the stimulus intensity corresponding to the intensity $S_1$ of the first image 25 is adjusted so as to be a constant value above the observer's visual threshold. This is done in order to ensure that the stimulus intensity is always constant with respect to an observer's visual threshold (constituting a zero threshold) in order that the relative stimulus intensity is identical for all observers participating in the test.

It should also be noted that during this initial period of the test, the observer is dark adapted because the presentation of dichoptic stimuli employed by the vergence test must be done in complete darkness. As is explained in greater detail below, particularly with reference to FIG. 8 of the drawings, the dark adaptation is accomplished by closing both of the optical shutters 18 and 19 and leaving the observer in a completely dark room for a period of approximately fifteen minutes. As a result, the observer's eyes relax and their axes rotate so as settle on the distance of dark vergence.

Thereafter, the vergence test itself is performed as is described in greater detail with reference to FIG. 3*b* of the drawings. Any results filed in respect of each observer are constantly updated consequent to each series of tests so that at the end of each series of tests the complete results file may be printed and analyzed.

Referring now to FIG. 3b, the principal operating steps associated with the vergence test are shown for a predetermined number of sequences of dichoptic stimuli. For each successive sequence, a pair of dichoptic stimuli is presented to the observer on the computer screen 10, each pair of stimuli comprising a first image which is fixed and a second image which moves relative to the first image. The first image is constituted by a vertical bar 31 having a small gap at its center whilst the second image is constituted by a dot 32 (see FIGS. 4a and 4b) which can appear on the left or right of the vertical bar. The time period between each sequence of dichoptic stimuli is randomly adjusted between approximately 5 to 7 sec. so that the observer cannot anticipate when exactly the next sequence of dichoptic stimuli will be presented on the computer screen 10 which, if permitted, would derogate from the accuracy and reliability of the test. Upon presenting each pair of dichoptic stimuli on the computer screen, the observer presses a control key in order to indicate whether the dot appears to the right or to the left of the vertical bars, the position of the dot being compensated for in a successive sequence of dichoptic stimuli so as to bring it into alignment with the vertical bars as seen by the observer. It should be understood that this process is dynamic and there is thus no need for the observer to indicate specifically when the two images appear to be aligned since, as they become closer and closer to each other from the observer's point of view, he will inevitably be constrained to pressing the right and left controls respectively. When this happens, the dot will be displaced on the screen a minimal amount so that, in fact, the position of the dot on the screen will oscillate around the point of alignment with the vertical bars, this oscillation or hunting corresponding to apparent alignment between the dot and the bars as seen by the observer.

It should also be noted that, in the event that the observer does not press either of the right or left responsive keys within a predetermined time period, no movement is effected to the dot and the same frame is repeated, albeit at a random time interval (as explained above) after the previous sequence of dichoptic stimuli.

After each sequence of dichoptic stimuli is presented on the screen, a trial counter is incremented, the whole loop being repeated in respect of successive sequences of dichoptic stimuli until a required number of sequences has been presented.

FIG. 3c is a flow diagram showing the principal operating steps in a method for determining the visual threshold of the observer. Thus, the first optical shutter 18 is opened and a dot is then displayed on the screen 10 for a period of 40 ms, following which there is a pause of 20 ms whereafter the first optical shutter 18 is closed and the second optical shutter 19 is opened. The vertical bars are now displayed for a period of 40 ms, following which there is a pause of a further 20 ms prior to closing the second optical shutter 19. As explained above with particular reference to FIGS. 1a to 1c of the drawings, this permits a pair of dichoptic stimuli to be presented whereby the first image is presented to the first eye and the second image to the second eye, such that each eye sees only one image even though both images are perceived as being presented together.

Dark vergence is the subtending angle of the eyes ($\theta_c$) where a subject is dark adapted or looks in an "empty field" (i.e. a shapeless visual field). It should be noted that even when there is a very short time interval between the presentation of successive images, providing the time interval is sufficiently short, the successive images will still be seen as a dichoptic stimulus even though both images are not, in fact, presented simultaneously.

It is, of course, desirable that the observer be displaced from the computer screen at a distance which is equal to the distance of dark vergence of the observer. In this case, the angle $\theta_c$ corresponding to the dark vergence angle subtended at the eye of the observer is equal to the angle $\theta_p$ subtended at the eye when the eyes of the observer are fixed on the computer screen.

Figure 4B:
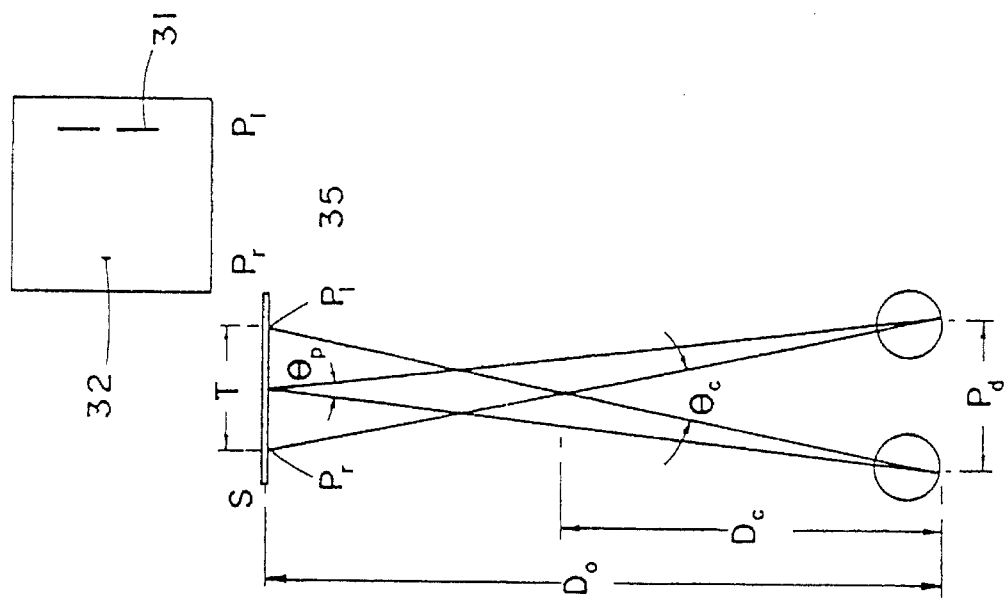
FIGS. 4a and 4b are schematic diagrams showing the effect on a viewed image of variation in the distance from the observer to the image plane.
Figure 4A:
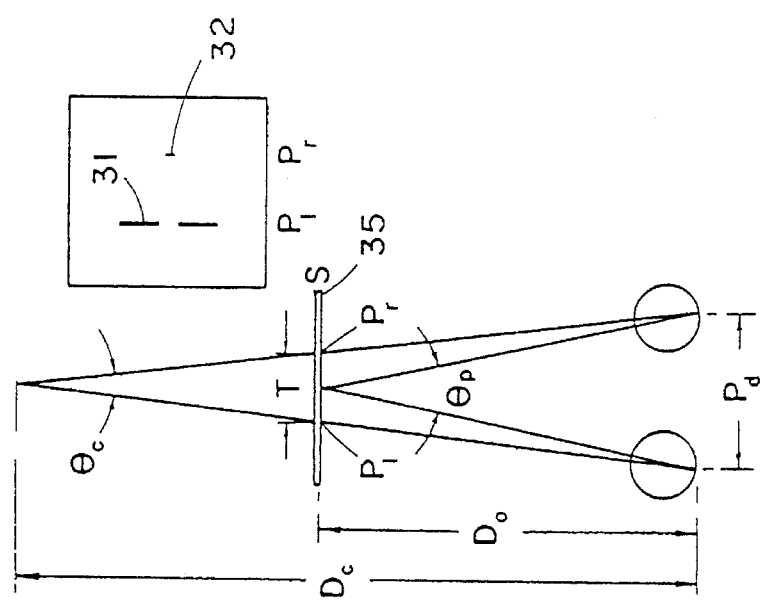

FIGS. 4a and 4b show, respectively, the situation when the distance of dark vergence denoted by $D_c$ is not equal to the distance from the observer to the computer screen denoted by $D_o$. Thus, as shown in FIG. 4a, $D_c > D_o$ whilst in FIG. 4b the reverse is the case and $D_c < D_o$. In both cases, it will be seen that the eyes subtend the same angle $\theta_p$ at the image plane 31 such that, in the first case, $\theta_p$ is $> \theta_c$ causing the dot 32 to appear to the right of the vertical lines 31, whilst in the second case shown in FIG. 4b the opposite is true and the dot 32 appears to the left of the lines 31.

In either case the actual distance T between the vertical lines 31 and the dot 32 may be used to calculate the distance of dark vergence $D_c$ in accordance with the formula:

$$D_c = \frac{P_d D_o}{P_d - f(T)}$$

where:

$D_c$ is the distance of dark vergence;

$P_d$ is the interpupillary distance;

$D_o$ is a distance from the observer to a viewing plane of the video display unit; and f(T) is a function of the measured displacement T between the two dichoptic images.

The function f(T) is determined by computing a polynomial regression through the displacement T between each pair of dichoptic images for the complete sequence of tests. The polynomial regression is computed based on the least mean square approximation. The function f(T) corresponds to the minimal value of the polynomial for the last six sequences of dichoptic stimuli. It should be noted that such an approach does not require the observer actually to indicate when the two images appear to be aligned: it is sufficient that he merely specifies if the dot 32 appears to the left of the lines 31 or vice versa. In practice this will cause hunting around the point of apparent alignment at the end of the test sequence, thereby permitting correct determination of the function f(T) as explained above.

Referring now to FIGS. 5 and 6, there is shown an apparatus depicted generally as 40 for determining dark vergence according to the invention. The apparatus 40 includes a computer 41 having a display monitor 42 and a keyboard 43. An observer (not shown) views the display monitor 42 through a telescopic tunnel 45 such that his distance from the display monitor 42 may be varied. The telescopic tunnel 45 is provided with a non-reflecting inner surface 46 so as to absorb stray reflections from the display monitor 42 and ensure that only light transmitted normal to the display monitor 42 reaches the eyes of the observer. Towards a front end 47 of the telescopic tunnel 45 there is provided an adjustable chin rest 48 and a headrest 49 having a concave shape for accommodating therein the observer's forehead, whereby the observer may sit in front of display monitor 42 in a predetermined and fixed relationship thereto throughout the sequence of tests as described above.

It will be understood that the test is performed in complete darkness: the only visual stimulation being the dichoptic stimuli themselves. As more and more dichoptic stimuli are thus presented, there exists the possibility that the observer will learn to judge the distance $D_o$ to the screen. As was mentioned above, Jaschinski-Kruza[3] reports that the subject's foreknowledge of the viewing distance has a small but nevertheless significant effect on the measured value of dark vergence. The telescopic tunnel 45 permits the distance $D_o$ from the observer to the screen to be varied throughout the test sequence, thereby preventing the observer from being able to gauge the distance $D_o$.

The telescopic tunnel 45 comprises two rectangular sections 50 and 51 each approximately 450 mm in length, the section 51 being slightly smaller than the section 50 so as to be slidably coupled therein.

At the front end 47 of the telescopic tunnel 45, there is provided a rigid support frame 52 having a pair of downwardly projecting side pieces 54 and 55 mounted on opposite sides of the telescopic tunnel 45 so as to provide a recess 56 in the front end 47 of the telescopic tunnel 45 within the rigid support frame 52. The keyboard 43 is hingedly attached to a lower end of the side pieces 54 and 55 via a hinge 57 so as to be rotatable into one of two operating positions in which either an upper surface 58 of the keyboard 43 is accessible or, alternatively, wherein a lower surface 59 thereof is accessible.

In an intermediate position, the keyboard 43 is rotated about the hinge 57 so as to be accommodated within the recess 56 such that the lower surface 59 of the keyboard 43 is flush with the front end 47 of the telescopic tunnel 45. Provided on the lower surface 59 of the keyboard 43 are push-button switches 60 and 61 (constituting control means) which the observer presses in order to indicate that the dot 32 lies to the right of the vertical lines 31 or to the left thereof, respectively.

FIG. 6 shows the apparatus 40 in a compacted state wherein the telescopic tunnel 45 is fully retracted and the keyboard 43 is rotated about the hinge 57 so that the lower surface 59 of the keyboard 43 lies flush with the front end 47 of the telescopic tunnel 45.

It is desirable that, prior to conducting the sequence of tests, no prior information is given to the observer as to the location of the display monitor 42 which, if allowed to occur, might bias his judgement. There is therefore provided an optically opaque shutter 64 which is mounted in front of rigid support frame 52 of the telescopic tunnel 45 for preventing the observer from seeing the display monitor 42 until the optically opaque shutter 64 is displaced.

Figure 7:
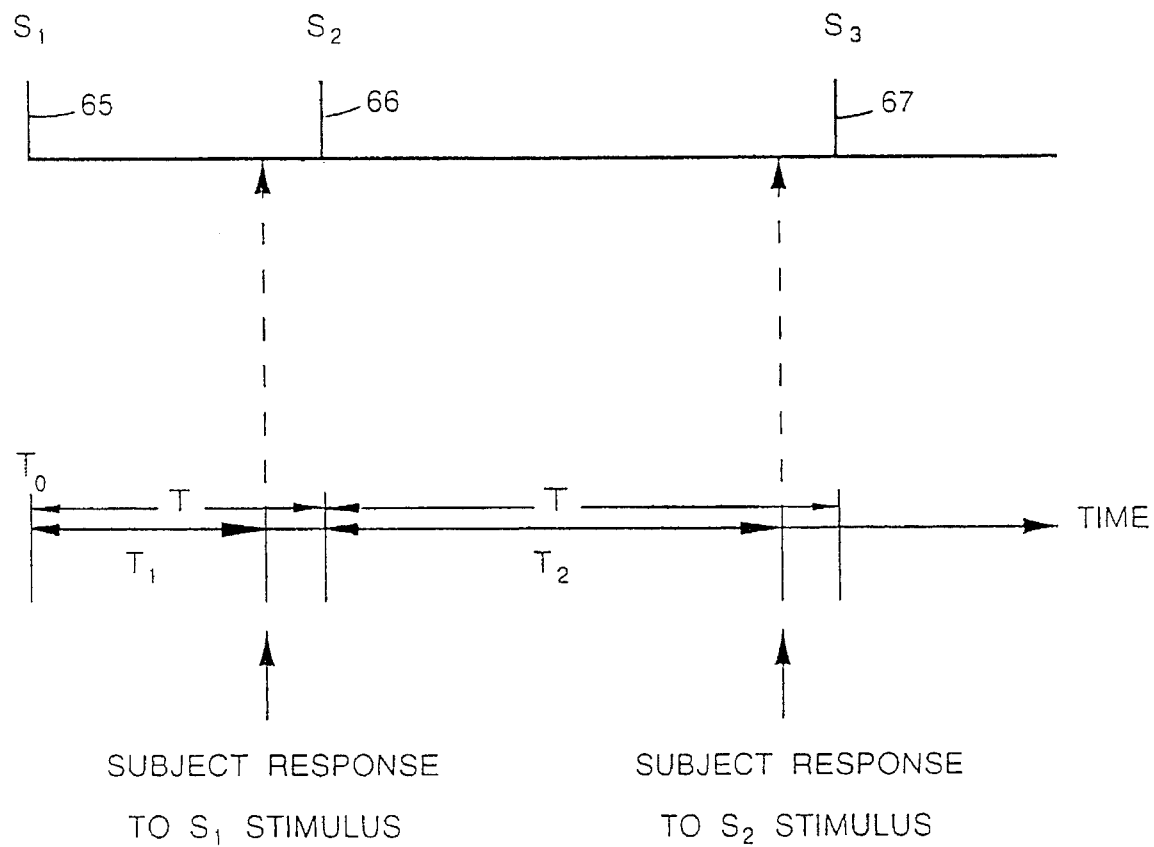
FIG. 7 shows schematically a timing diagram relating to the elapsed time between the presentation of successive dichoptic stimuli.

Referring to FIG. 7 there is shown a timing diagram relating to the display of successive dichoptic stimuli on the display monitor. Thus, at time $T_0$ a first pair of images designated 65 is displayed comprising, in reality, two separate images which are separately displayed in very quick succession. As explained above, upon seeing the second image, the observer presses one of the two push-button switches 60 or 61 so as to indicate to which side of the vertical lines 31 the dot 32 appears. An intersequence period generator (shown functionally in FIG. 3b and constituting a randomizing means) is responsive to a reaction time $T_1$ of the observer between the second of the two dichoptic stimuli being presented on the video unit and the observer pressing one of the two push-button switches 60 or 61, in order to calculate a random time period T from the instant of the observer pressing one of the two push-button switches 60 or 61 and the subsequent display of the next sequence of dichoptic stimuli 66. Likewise, a third sequence of dichoptic stimuli 67 is displayed a random time period T after the observer presses one of the push-button switches 60 or 61 consequent to the second pair of dichoptic stimuli 66 appearing on the display monitor.

In the event that the observer does not press either of the two push-button switches 60 or 61 within a predetermined time period, the same sequence exactly of dichoptic stimuli is again presented on the display monitor.

In practice, the random time period T varies between 5 to 7 sec. so as to prevent the observer from being able to estimate when a successive sequence of dichoptic stimuli is about to be presented on the display monitor.

Figure 8:
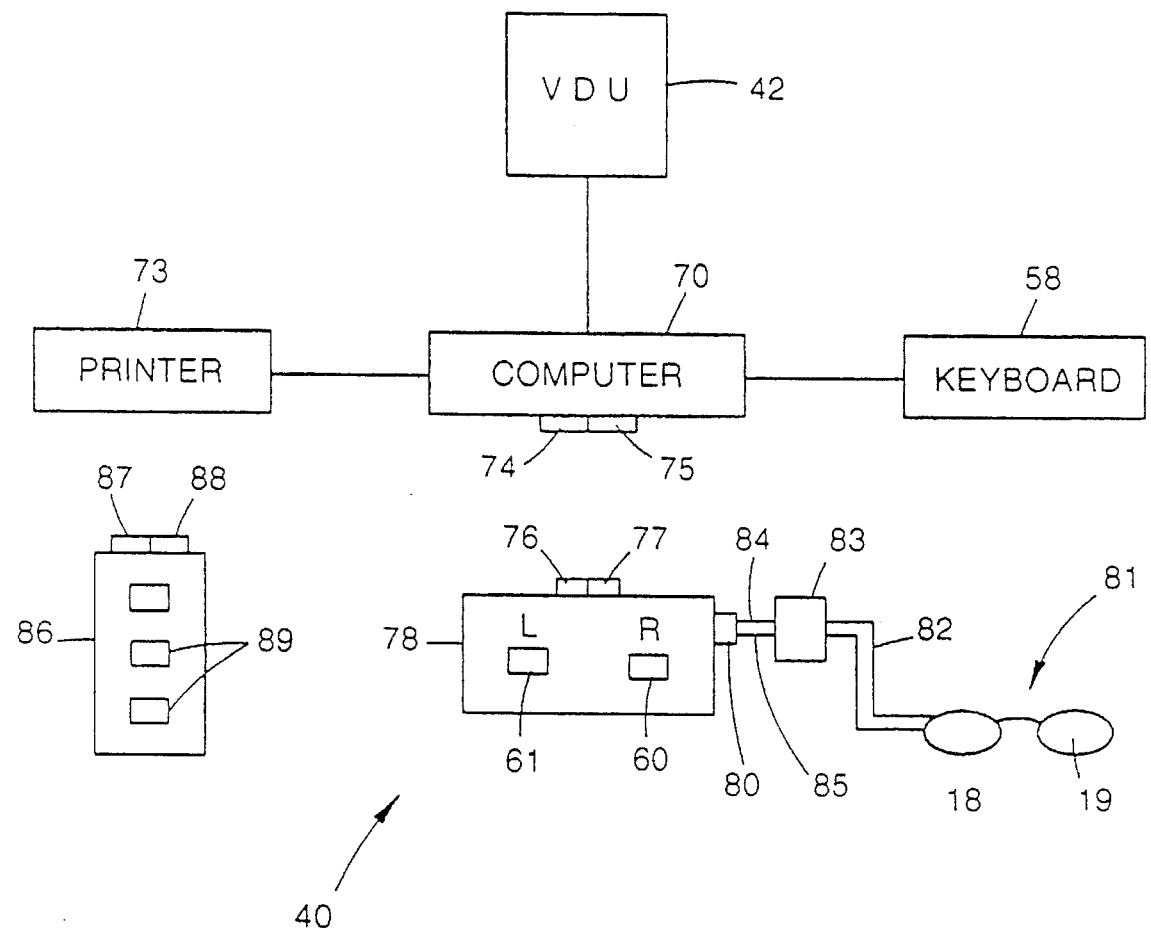
FIG. 8 is a block diagram showing functionally the apparatus illustrated in FIG. 4.

Referring to FIG. 8 there is shown a block diagram of the apparatus 40 shown pictorially in FIGS. 5 and 6. To the extent that the components shown in FIG. 8 have already been described with reference to FIGS. 5 and 6, identical reference numerals will be employed.

Thus, the apparatus 40 comprises a computer 70, typically constituted by a personal computer having an integral hard disk and a floppy disk drive such that on either the hard disk or the floppy disk data can be permanently recorded and archived. The keyboard 58 and the VDU 42 are connected to the computer 70 in the usual manner, as is a printer 73 for printing test results stored within the computer 70.

Also coupled to the computer 70 is an infrared transmitter 74 and an infrared receiver 75 permitting bi-directional data communication to an infrared receiver 76 and from an infrared transmitter 77 of a control unit 78. The control unit 78 is battery powered and has a pair of output jack sockets designated as 80 to which the internal battery (not shown) is connected. The right and left push-button switches 60 and 61, respectively, are provided within the control unit 70, the arrangement being such that when one of the push-button switches 60 or 61 is pressed, a corresponding infrared signal is sent via the infrared transmitter 77 so as to be received by the infrared receiver 75 of the computer 70. The computer 70 is responsive to the received signal for moving the dot 32 relative to the vertical lines 31 (FIGS. 4a and 4b) as described above.

The first and second optical shutters 18 and 19 are provided within a pair of spectacles 81, each of the optical shutters 18 and 19 being connected, via respective twin-wire leads designated schematically as 82 to a portable adapter unit 83. The adapter unit 83 contains its own small battery (not shown) as well as suitable changeover circuitry whereby when the left optical shutter 18 is connected to the battery the right optical shutter 19 is disconnected therefrom and vice versa.

Each of the twin-wire leads 82 is connected via a suitable switch (not shown) to a respective jack plug 84 and 85 such that when the jack plugs 84 and 85 are plugged into the corresponding jack sockets 80 of the control unit 78, the internal battery within the adapter 83 is disconnected from the twin-wire leads 82 and the internal battery of control unit 78 is connected thereto instead.

A hand-held remote control unit 86 is also provided having an infrared receiver 87 and an infrared transmitter 88 and being further provided with a plurality of control buttons 89 whereby data can be transmitted to the computer 70 and received therefrom.

In use, a technician or other competent person may use either the keyboard 58 or, alternatively, the hand-held unit 86 to feed in to the computer 70 relevant data relating to a subject being tested. The subject wears the spectacles 81 in which the optical shutters 18 and 19 are constituted by suitable liquid crystal elements, both of the twin-wire leads 82 being connected to the battery within the adapter 83 so that the liquid crystal elements are black in both optical shutters 18 and 19. By such means, the subject may be dark-adapted even before a series of tests is commenced, it then being necessary only to connect the jack plugs 84 and 85 to the corresponding jack sockets 80 of the control unit 78, whereupon the twin-wire leads 82 are disconnected from the battery inside the adapter 83 and are coupled, instead, via the changeover switch within the adapter 83 to the battery inside the control unit 78. The changeover switch, in its initial state, ensures that the optical shutter 18 is disconnected from the battery and is therefore clear, whilst the right optical shutter 19 remains connected to the battery and therefore remains dark: this being the situation described above with reference to FIG. 1*a* of the drawings.

Appropriate header data identifying the subject's name, age and so on are entered into the computer 70 by the technician using either the hand-held control unit 86 or the keyboard 58. Upon completion of a series of tests, or indeed throughout the tests themselves, additional data may, if required, be entered as required. At the conclusion of the series of tests, the relevant computations are performed by the computer 70 in accordance with a program stored therein, the test results then being printed by the printer 73.

It will be appreciated that data communication via infrared transmission is well known in the art and is employed, for example, in television remote controllers and the like, there being no need therefore to describe this feature in greater detail.

FIG. 9*a* is a schematic optical ray diagram showing an observer 90 who is seated a substantially fixed distance $D_o$ from a computer screen 91. In the event that the distance $D_o$ is not equal to the distance dark vergence $D_c$ then, as explained above with reference to FIGS. 4*a* and 4*b* of the drawings, the angle $\theta_p$ subtended by the eyes of the observer at the screen 91 will not be equal to the dark vergence angle $\theta_c$. In this case the extraocular muscles of the eyes are not completely relaxed, thereby resulting in operator fatigue. Such fatigue can be reduced significantly by providing the operator with a pair of spectacles 95 comprising respective prismatic elements 96 for bending the light 97 transmitted by the pixels of the computer monitor 91 so that the resulting angle subtended by the eyes 98 at the plane of the computer monitor 91 is equal to the angle of dark vergence $\theta_c$.

FIG. 9*b* is an enlarged partial feature of FIG. 9*a* showing in greatly magnified detail the principle of operation of the spectacles 95. Thus the ray of light 97 is bent by the prismatic element 96 so that to the eye 98 the ray of light 97 appears to emanate from the point of dark vergence at a distance $D_c$ from the operator 90.

It is clear that, even when such spectacles 95 are provided, the distance $D_o$ from the observer 90 to the computer screen 91 must thereafter be maintained substantially constant. To this end, there is shown in FIG. 9*c* on top of the computer monitor 91 a battery operated alarm unit 100 which transmits an ultrasonic signal towards the operator 90 so as to be reflected thereby and received by the alarm unit 100. By measuring an elapsed time between transmission and subsequent reception of the ultrasonic signal, the distance from the alarm unit 100, and hence the computer monitor 91 to the operator 90 may be measured. The measured distance is compared with the distance of dark vergence in respect of the operator which, having previously been determined is programmed into the alarm unit 100, so as to provide a visual or audible warning in the event that the measured distance differs from the measured dark vergence by more than a predetermined threshold. By such means, the operator 90 knows to move his head into a position whereby the alarm ceases thereby significantly reducing problems associated with operator fatigue. The threshold which is programmed into the alarm unit 100 is sufficiently large to permit the operator 91 sufficient variation in the range of his distance from the computer monitor 91 so as to avoid continual alarm signals being generated by the alarm unit 100.

Figure 10:
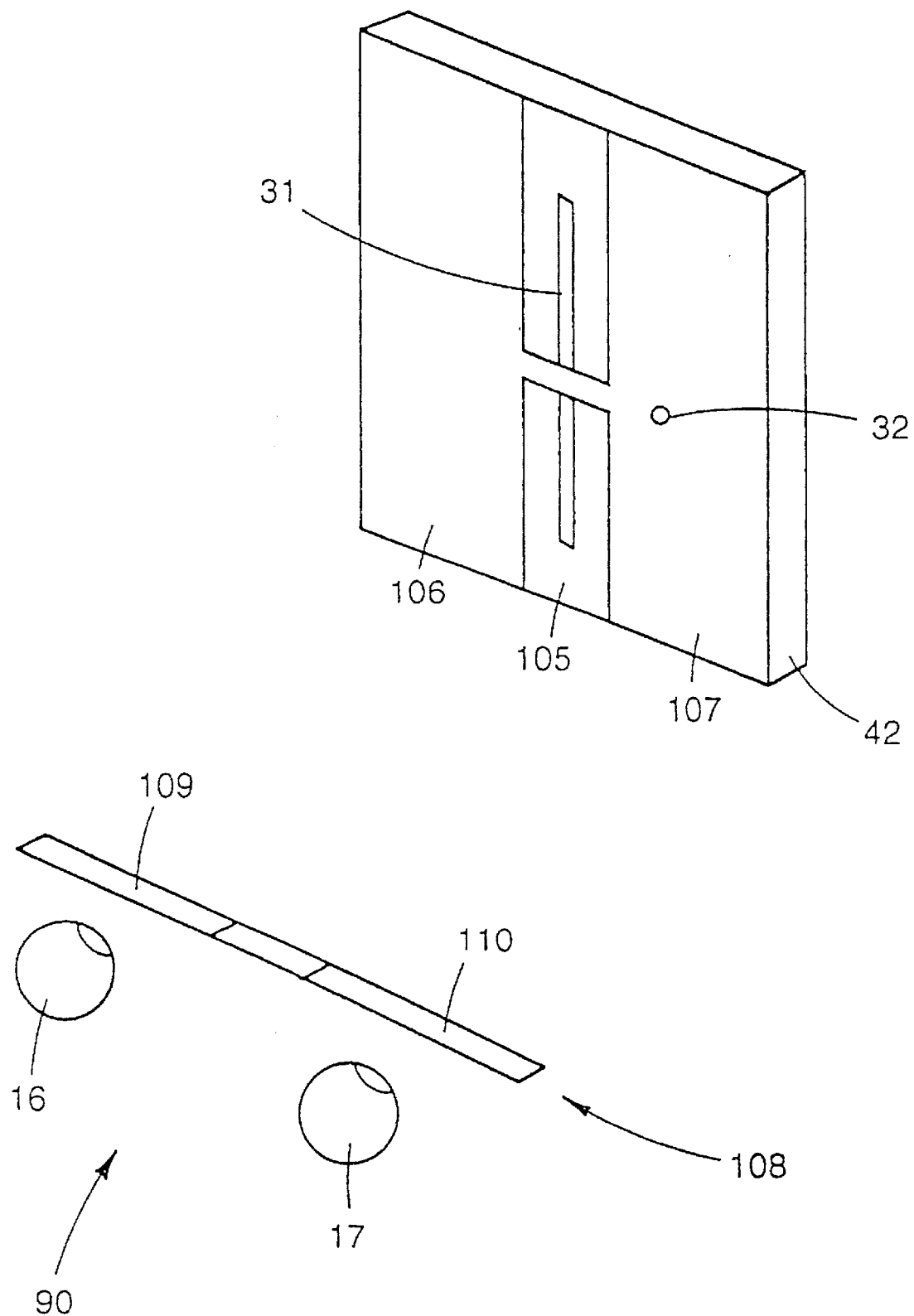
FIG. 10 is a pictorial representation showing an alternative method for presenting dichoptic stimuli according to the invention using polarizing elements.

Referring now to FIG. 10 of the drawings, there is shown pictorially an alternative approach to presenting dichoptic stimuli on the VDU 42. To a small centrally disposed vertical strip of the VDU there is affixed a first polarizing screen 105 so as to cover the first image constituted by the vertical lines 31. On either side of the first polarizing screen 105 are affixed corresponding second polarizing screens 106 and 107 both having identical directions of polarization which are perpendicular to the direction of polarization of the first polarizing screen 105.

The observer 90 wears a pair of spectacles 108 having respective polarizing elements 109 and 110 which are adjusted for passing light from the vertical line 31 and from the dot 32, respectively. Under these conditions, the left eye 16 sees only the vertical line 31 whilst the right eye sees only the dot 32. At the same time, both eyes are prevented from seeing the other image because the polarizing elements act as filters which totally block the passage of light whose direction of polarization is perpendicular to that of the polarizing elements themselves.

It is also envisaged within the framework of the invention to employ a color monitor, whereupon the vertical line 31 as a red image and the dot 32 as a green image, or vice versa. The required image separation may then be achieved by disposing corresponding colored filters in front of the respective eyes of the observer.

In both of the above configurations, the first and second images may, in fact, be presented simultaneously. However, strictly speaking, in a raster type VDU, the images are in fact presented successively depending on the scan rate of the VDU.

There is thus provided in accordance with the invention a method and apparatus for presenting successive sequences of dichoptic stimuli on a video display unit. Such a method and apparatus may be used to determine the dark vergence of a computer operator whereupon suitable spectacles may be prescribed for the operator to compensate for differences between the measured dark vergence and his comfortable operating distance from the computer monitor. An alarm unit provided on top of the computer monitor, may be provided so as to provide a visual or audible warning in the event that the measured dark vergence differs form the operator's distance from the computer monitor by more than a predetermined threshold.

I claim:

1. A method for presenting two successive images having respective first and second unequal intensities on a video display unit as a dichoptic stimulus of substantially equal intensity, comprising the steps of:

(a) displaying a first one of the images at said first intensity on the video display unit for a first predetermined time interval so as to be seen by a first eye of an observer only, (b) suppressing any after image of the first image to a second eye of the observer by:

(b1) extinguishing the first image, (b2) inhibiting the second eye from seeing the video display unit for a predetermined period of time, and (b3) attenuating any residual after image of the first image using a neutral density filter having a predetermined attenuation factor; and (c) displaying a second one of the images on the video display unit so as to be seen by the second eye of the observer only at said first intensity by:
(c1) displaying the second one of the images at said second intensity equal to said first intensity multiplied by said predetermined attenuation factor.

2. A method for presenting two successive images having respective first and second unequal intensities on a video display unit as a dichoptic stimulus of substantially equal intensity, comprising the steps of:

(a) displaying a first one of the images at said first intensity on the video display unit for a first predetermined time interval so as to be seen by a first eye of an observer only, (b) suppressing any after image of the first image to a second eye of the observer by:
(b1) extinguishing the first image,
(b2) inhibiting the second eye from seeing the video display unit for a predetermined period of time, and
(b3) attenuating any residual after image of the first image using a polarizer having a predetermined attenuation factor; and (c) displaying a second one of the images on the video display unit so as to be seen by the second eye of the observer only at said first intensity by:
(c1) displaying the second one of the images at said second intensity equal to said first intensity multiplied by said predetermined attenuation factor.

3. A method for presenting two successive images on a color video display unit as a dichoptic stimulus of substantially equal intensity, comprising the step of:

(a) displaying a first one of the images as a red image at a predetermined intensity on the video display unit for a first predetermined time interval so as to be seen by a first eye of an observer only, (b1) disposing in front of the first eye a red filter;

(b2) disposing in front of the second eye a green filter; and (c) displaying a second one of the images as a green image on the video display unit for a second predetermined time interval so as to be seen by the second eye of the observer only at said predetermined intensity whereby each eye sees only one of the respective images.

4. A method for determining a dark vergence of an observer, comprising the steps of:

(a) measuring an interpupillary distance of the observer, (b) presenting a sequence of two successive images on a video display unit each for respective first and second time intervals, so as to be seen by the observer as a dichoptic stimulus of substantially equal intensity relative to a predetermined visual threshold of the observer such that a first one of the images is stationary and a second one of the images may be moved by illuminating different pixels of the video display unit, (c) for each sequence of images presented on the video display unit, moving the second one of the images until both images appear to the observer to be aligned, (d) measuring any actual displacement between the two images, and (e) calculating a distance of dark vergence according to the formula:

$$D_c = \frac{P_d D_o}{P_d - f(T)}$$

where:

$D_c$ is the distance of dark vergence;
$P_d$ is the interpupillary distance;
$D_o$ is a distance from the observer to a viewing plane of the video display unit; and
$f(T)$ is a polynomial function of the measured displacement T between the two dichoptic images which approximates the measured displacement T for at least a latter portion of said sequence of images.

5. The method according to claim 4, wherein prior to performing step (c) there is further includes step of preventing the observer from gauging the distance $D_o$ from the observer to the viewing plane of the video display unit.

6. The method according to claim 5, wherein the step of preventing includes disposing an optically opaque element in front of the video display unit prior to performing step (c).

7. The method according to claim 4, wherein for each sequence of dichoptic images the observer indicates any apparent misalignment between the two images whereby in a successive sequence of images, the second image may be moved so as to compensate for said apparent misalignment.

8. The method according to claim 4, wherein step (c) includes the steps of:

(c1) displaying a first pair of images on the video display unit so as to be seen by respective eyes of the observer, (c2) the observer indicating an apparent misalignment between the first pair of images, and (c3) displaying a second pair of images at a random time interval T after the observer indicates said apparent misalignment between the first pair of images.

9. The method according to claim 8, wherein after step (c2) there is further included the step of:

(c3') measuring a reaction time $T_1$ between displaying said first pair of images and the observer indicating said apparent misalignment;

the time interval T being a quasi-random function larger than and independent of the reaction time $T_1$ of the observer between specified lower and upper limits.

10. The method according to claim 4, wherein each of the images displayed on the video display unit has a predetermined intensity equal to a predetermined level above the measured visual threshold of the observer.

11. An apparatus for presenting two successive images on a video display unit as a dichoptic stimulus of substantially equal intensity, the apparatus comprising:

a video display unit having a plurality of pixels, first and second optical shutters disposed between the video display unit and respective eyes of the observer, first control means coupled to the video display unit and to the first and second optical shutters for illuminating predetermined ones of said pixels so as to present a first image to a first eye of an observer at a predetermined intensity, for illuminating predetermined ones of said pixels so as to display a second image to a second eye of the observer at an intensity equal to said predetermined intensity multiplied by a predetermined attenuation factor, for opening the first optical shutter and closing the second optical shutter whilst the first image is illuminated and for closing the first optical shutter and opening the second optical shutter whilst the second image is illuminated, attenuation means disposed between the video display unit and a second eye of the observer so as to attenuate by said predetermined attenuation factor an image presented by the video display unit to the second eye of the observer, and extinguishing means coupled to the video display unit for extinguishing the first image.

12. The apparatus according to claim 11, wherein the attenuation means is a neutral density filter.

13. The apparatus according to claim 11, wherein the attenuation means is a polarizer.

14. The apparatus according to claim 11, further including:

second control means operable by the observer for indicating an apparent displacement between the two images so as to produce a corresponding signal;

the first control means being coupled to the second control means and being responsive to said signal for illuminating different ones of said pixels so as effectively to move the second image relative to the first image in a direction to correct said apparent misalignment.

15. The apparatus according to claim 14, wherein the second image may be moved to the right or left of the first image and the second control means includes right and left indication means for indicating the corresponding misalignment between the first and second images.

16. The apparatus according to claim 15, wherein:

the video display unit is a display monitor of a computer, and the second control means is integrally fitted to a keyboard of the computer.

17. The apparatus according to claim 14, further including preventing means for preventing the observer from gauging a distance $D_o$ from the observer to the video display unit.

18. The apparatus according to claim 17, wherein the preventing means includes a telescopic tunnel disposed between the video display unit and the observer and having a non-reflecting inner surface, the telescopic tunnel permitting variation of a distance between the observer and the video display unit.

19. The apparatus according to claim 18, further including a displaceable optically opaque shutter in front of the telescopic tunnel for preventing the observer from seeing the video display unit until the optically opaque shutter is displaced.

20. The apparatus according to claim 18, wherein:

the video display unit is a display monitor of a computer, a keyboard of said computer is hingedly attached to a front end of the telescope tunnel so as to allow rotation of the keyboard whereby it may be accommodated within a recess of said front end of the telescopic tunnel such that a lower surface of the keyboard is flush with the front end of the telescopic tunnel.

21. The apparatus according to claim 20, wherein the second control means is integrally fitted to the lower surface of the keyboard.

22. The apparatus according to claim 20, wherein the lower surface of the keyboard has a recess for accommodating therein the second control means when not in use.

23. The apparatus according to claim 14, wherein the first control means is responsively coupled to the second control means for producing said successive images a predetermined time interval after operation of the control means.

24. The apparatus according to claim 23, further including randomizing means coupled to the second control means and responsive to an elapsed time between display of a pair of images on the video display unit and the production of said corresponding signal by the second control means for determining said predetermined time interval as a random function of said elapsed time.

25. The apparatus according to claim 14, further including computing means responsive to an actual displacement between the first and second images when they appear aligned to the observer for computing a distance of dark vergence of the observer according to the formula:

$$D_c = \frac{P_d D_o}{P_d - f(T)}$$

where:

$D_c$ is the distance of dark vergence;

$P_d$ is the interpupillary distance;

$D_o$ is a distance from the observer to a viewing plane of the video display unit; and f(T) is a function of the measured displacement T between the two dichoptic images.

26. The apparatus according to claim 25, wherein the second control means is remotely coupled to the computing means for effecting bi-directional data communication therewith.

27. An apparatus for presenting two successive images on a video display unit as a dichoptic stimulus of substantially equal intensity, the apparatus comprising:

a video display unit having a plurality of pixels, control means coupled to the video display unit for illuminating predetermined ones of said pixels so as to present respective first and second images to respective first and second eyes of an observer at a predetermined intensity, first polarizing means associated with the video display unit for polarizing the first image in a first direction, second polarizing means associated with the video display unit for polarizing the second image in a second direction perpendicular to the first direction, third polarizing means disposed between the first eye of the observer and the first polarizing means and adjusted for passing light from the first image only, and fourth polarizing means disposed between the second eye of the observer and the second polarizing means and adjusted for passing light from the second image only.

28. An apparatus for presenting two successive images on a video display unit as a dichoptic stimulus of substantially equal intensity, the apparatus comprising:

a color video display unit having a plurality of pixels, control means coupled to the video display unit for illuminating predetermined ones of said pixels so as to present respective first and second images to respective first and second eyes of an observer at a predetermined intensity, a first filter disposed between the first eye of the observer and the color video display unit for passing light from the first image only, and a second filter disposed between the second eye of the observer and the color video display unit for passing light from the second image only.

29. A method for correcting for dark vergence of an observer of a video display unit disposed a substantially fixed distance from the observer so as to subtend a substantially fixed angle $\theta_p$ at the observer's eyes, comprising the steps of:

measuring a dark vergence angle $\theta_c$ of the observer, disposing correcting lenses in front of the observer's eyes so as to bend light emitted by the video display unit so that the light subtends the dark vergence angle $\theta_c$ at the eyes of the observer.

30. A method for interactively monitoring the distance between an observer and a video display unit disposed a variable distance from the observer, so as to warn the observer if the distance differs from the observer's dark vergence distance by more than a predetermined value, the method comprising the steps of:

measuring the dark vergence distance of the observer, measuring the distance between the observer and the video display unit, comparing the measured distance with the measured dark vergence distance, and automatically warning the observer if the measured distance differs from the measured dark vergence distance by more than said predetermined value.

31. An apparatus for interactively monitoring the distance between an observer and a video display unit disposed a variable distance from the observer, so as to warn the observer if the distance differs from the observer's dark vergence distance by more than a predetermined value, the apparatus comprising:

storage means for storing therein the dark vergence distance of the observer and said predetermined value, measuring means for determining the distance between the observer and the video display unit, comparator means coupled to the storage means and to the measuring means for comparing the measured distance with the stored dark vergence distance and producing a warning signal if the measured distance differs from the stored dark vergence distance by more than said predetermined value, and indication means coupled to the comparator means and responsive to the warning signal for producing an indication to the observer that he should shift his position relative to the display unit.

\* \* \* \* \*